(12) United States Patent
Hedlund et al.

(10) Patent No.: US 6,395,750 B1
(45) Date of Patent: May 28, 2002

(54) DRUGS FOR THE TREATMENT OF MALIGNANT TUMORS

(75) Inventors: Gunnar Hedlund, Lund; Karl Jansson, Dalby; Stig Jönsson, Lund; Anders Björk, Bjärred, all of (SE)

(73) Assignee: Active Biotech AB, Lund (SE)

( * ) Notice: Subject to any disclaimer, the term of this patent is extended or adjusted under 35 U.S.C. 154(b) by 0 days.

(21) Appl. No.: 09/694,757

(22) Filed: Oct. 24, 2000

Related U.S. Application Data

(60) Provisional application No. 60/212,816, filed on Jun. 21, 2000, and provisional application No. 60/161,407, filed on Oct. 25, 1999.

(30) Foreign Application Priority Data

Oct. 25, 1999 (SE) .............................. 9903838
Jun. 21, 2000 (SE) .............................. 002320

(51) Int. Cl.⁷ ................. A61K 31/47; C07D 215/36; C07D 215/16; C07D 215/38
(52) U.S. Cl. ............... 514/312; 514/313; 546/153; 546/155; 546/159
(58) Field of Search ............... 514/313, 314, 514/312; 546/156, 153, 155, 159

(56) References Cited

FOREIGN PATENT DOCUMENTS

| | | |
|---|---|---|
| EP | 0 059 698 | 9/1982 |
| GB | 2 290 786 | 1/1996 |
| WO | 92 18483 | 10/1992 |
| WO | WO 9218483 | * 10/1992 |
| WO | 95 24395 | 9/1995 |

OTHER PUBLICATIONS

Kelly, D. F. et al; "Polyarteritis in the Dog: A Case Report"; *The Veterinary Record*, vol. 92, pp. 363–366; Apr. 7, 1973.

Harcourt, R.A.; "Papers and Articles: Polyarteritis in a Colony of Beagles"; *The Veterinary Record*; vol. 102; pp. 519–522; Jun. 17, 1978.

(List continued on next page.)

*Primary Examiner*—Alan L. Rotman
*Assistant Examiner*—Binta Robinson
(74) *Attorney, Agent, or Firm*—Browdy and Neimark, P.L.L.C.

(57) ABSTRACT

The invention relates to a method for the treatment of tumors in mammals by the administration of compounds of the general formula (I)

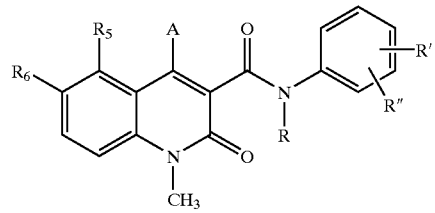

wherein A is $O_{41}$ or $NR_{42}R_{43}$ wherein $R_{41}$ is hydrogen or a pharmaceutically acceptable inorganic or organic cation, or $COR_A$ wherein $R_A$ is alkyl and aryl; $R_{42}$ and $R_{43}$ are hydrogen, C1–C4-alkyl, cyclopropyl, cyclopentyl or cyclohexyl; or $R_{42}$ is benzyl or phenethyl, optionally mono- or disubstituted by methyl, iso-propyl methoxy, fluoro, chloro, bromo, dimethylamino, trifluoromethyl or nitro and $R_{43}$ is hydrogen; or $R_{42}$ and $R_{43}$ form a 5- or 6-membered ring; or $R_{42}$ is $COR_B$ wherein $R_B$ is alkyl or aryl, —CH$_2$N(CH$_3$)$_2$ or —CH$_2$CH$_2$COOH or $COR_B$ is a 2-acyloxymethylbenzoyl group

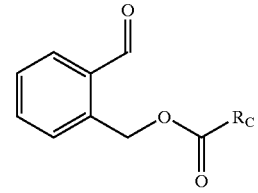

wherein $R_C$ is methyl, ethyl, phenyl or benzyl; $R_{42}$ is $COOR_D$ wherein $R_D$ is C1–C4-alkyl, phenyl or benzyl; or $R_{42}$ is —CH$_2$OCO-tert.-butyl or $R_{42}$ is $CONR_FR_G$ wherein $R_F$ and $R_G$ are C1–C4-alkyl; or $R_{42}$ is $CXN$-$HR_E$ wherein X is O or S and $R_E$ is C1–C4-alkyl, C2–C4-alkyl functionalized with an tertiary amino group, or phenyl, optionally functionalised with a p-chloro group; or $R_{42}$ is $CH_2NR_HR_I$ wherein $R_H$ and $R_I$ are C1–C4-alkyl and $R_H$ and $R_I$ form a morpholine ring and $R_{43}$ is hydrogen, C1–C2-alkyl or cyclopropyl; R is hydrogen, C1–C4-alkyl or allyl; with the proviso that R is not hydrogen when A is $OR_{41}$; R' is hydrogen, methyl, methoxy, fluoro, chloro, bromo, cyano, nitro, azido, trifluoromethyl, or $OCH_xF_y$, wherein x=0–2, y=1–3 with the proviso that x+y=3; and that R' is not hydrogen when R is methyl and A is $OR_{41}$; R" is hydrogen, fluoro or chloro, with the proviso that R" is fluoro or chloro only when R' is fluoro or chloro; $R_5$ is hydrogen, C1–C3-alkyl; methoxy, ethoxy, thio-C1–C3-alkyl fluoro, chloro, bromo, trifluoromethyl, nitro, amino, dimethylamino or $OCH_xF_y$, or $OCH_2CH_xF_y$ wherein x=0–2, y=1–3 with the proviso that x+y=3 and that $R_5$ is not fluoro or amino when A is $OR_{41}$; and that $R_5$ is hydrogen only when A is $NR_{42}R_{43}$ and R' is trifluoromethyl; $R_6$ is hydrogen; or $R_5$ and $R_6$ taken together are methylenedioxy, or any tautomer, optical isomer or racemate thereof. The invention also comprises novel compounds, therapeutic compositions and processes for the preparation of the compounds of formula I.

66 Claims, No Drawings

OTHER PUBLICATIONS

Ichikawa, T. et al; "The Antitumor Effects of the Quinoline–3–Carboxamide Linomide on Dunning R–3327 Rat Prostatic Cancers"; *Cancer Research*; vol. 52, pp. 3022–3028, Jun. 1, 1992.

Abstract, JP07224040, "Preparation of 3–carbamoyl–1, 2–d–dihydro–2–oxoquinoline derivatives as immunomodulators, antiinflammatory agents, and anticancer agents", (1995).

Abstract, JP07252228, "Preparation of 2–oxoquinoline derivatives as immunomodulators and antiinflammatory and anticancer agents", (1996).

Wit et al., "EORTC Phase II Study of Daily Oral Linomide in Metastatic Renal Cell Carcinoma Patients with Good Prognostic Factors"; *European Journal of Cancer*, (1997) vol.33, No.3, pp.493–495, Great Britain.

* cited by examiner

DRUGS FOR THE TREATMENT OF MALIGNANT TUMORS

CROSS REFERENCES TO RELATED APPLICATIONS

This application claims the benefit of U.S. provisional applications No. 60/161,407 filed Oct. 25, 1999 and No. 60/212,816 filed Jun. 21, 2000 respectively.

FIELD OF THE INVENTION

The present invention relates to a method for the clinical treatment of a plurality of malignant tumours, especially in solid form, in mammals by the administering of quinoline derivatives. Furthermore, the present invention relates to structurally novel quinoline derivatives, to methods for their preparation and to compositions containing them. The types of cancer that are especially inhibited by the quinoline derivatives of the present invention include, for example, breast cancers, colon cancers, Kaposi's sarcoma, lung cancers, ovarian cancers, prostatic cancers, and skin cancers. More particularly, the present invention relates to quinoline derivatives suitable for treatment of and preventing the development of prostatic cancer, and for preventing and treatment of the metastases of prostatic cancer.

BACKGROUND OF THE INVENTION

Solid tumours, primary or metastases consist of several types of cells where the tumour cells are the pivotal cell type and the driving force. When microtumours reach a certain size, the requirement of nutrition cannot be satisfied by plain diffusion. New vessels penetrate the tumour establishing a microenvironment providing the tumour with optimal nutrition for further proliferation and growth. This tumour induced angiogenesis, inducing proliferation, migration and differentiation of normal endothelial cells from nearby small blood vessels, is a prerequisite for the growth of solid tumours. In concordance the inhibition of angiogenesis results in an effective inhibition of growth of solid tumours.

Solid tumours spread by penetrating tissue borders and give rise to daughter cell colonies or metastases. Single tumour cells or small cell aggregates spread by the blood or the lymph system to distant sites. In this process the tumour cells are vulnerable and can be extinguished by natural killer (NK) cells, a distinct type of cytotoxic lymphocytes. Enhanced activity or an increased number of NK cells reduce or inhibit the metastasising process in solid tumour disease.

Prostatic cancer is a malignant tumour disease that spreads to distant sites as tumour metastases and comprises tumours with great dependence of neovascularisation. Prostatic cancer has long been a major affliction of men, and it is becoming more common and dangerous as the population ages. It is an adenocarcinoma that is second only to lung cancer in mortality. Prostate cancer currently accounts for about 35,000 deaths each year in the United States alone. To the present time, there are no effective preventive or treatment methods for prostatic cancer. When the cancer is in its early, hormone-dependent stage, it is commonly treated by orchiectomy or chemical castration. In the later stages of prostatic cancer, the disease becomes hormone-independent and metastasises widely, usually first into the skeleton. Treatment for advanced disease initially involves hormonal manipulations and palliative radiotherapy or treatment with cytostatic agents. These strategies have proven to be of marked clinical benefit in terms of symptomatic relief but there are no effective methods, which can put prostatic cancer into remission in that stage. The use of cytotoxic agents in the management of hormone-resistant advanced prostate cancer remains poorly defined. A few single agents have become "standard therapy", although demonstration of their efficacy, by contemporary standards, is lacking. Thus, prostatic cancer is not only relatively common, but is refractory to treatment once the disease crosses into the hormone-independent stage.

In U.S. Pat. No. 4,547,511 and in EP 59,698 some derivatives of N-aryl-1,2-dihydro-4-amino-1-alkyl-2-oxo-quinoline-3-carboxamide and N-aryl-1,2-dihydro-4-hydroxy-1-alkyl-2-oxo-quinoline-3-carboxamide are claimed as enhancers of cell-mediated immunity. Roquinimex (Merck Index $12^{th}$ Ed., No. 8418; Linomide®, N-methyl-N-phenyl-1,2-dihydro-4-hydroxy-1-methyl-2-oxo-quinoline-3-carboxamide) has been reported to have antitumour effects on Dunning R-3327 rat prostatic cancers (1).

Some 5-substituted N-aryl-1,2-dihydro-4-hydroxy-1-alkyl-2-oxo-quinoline-3-carboxamides effective in the treatment of diseases resulting from autoimmunity and pathologic inflammation are known from U.S. Pat. No. 6,077,851, U.S. Ser. Nos. 09/352,886 and 09/352,887.

Roquinimex, a compound with shown anti-angiogenic and pro NK lymphocyte activities also induce pro-inflammatory side effects in humans that was emphasised when treating patients with renal cell carcinoma (2). Roquinimex in this study was poorly tolerated, with 40% of the patients being withdrawn or having dose reductions due to adverse events, mostly influenza-like symptoms of myalgia, arthralgia and fatigue. Several cases of pericarditis and neuropathy were also observed.

Pro-inflammatory effects induced by roquinimex are efficiently monitored in the beagle dog. Roquinimex induces the beagle pain syndrome characterised by fever, myalgia, arthralgia as well as arteritis (3, 4).

DESCRIPTION OF THE INVENTION

A primary objective of the present invention is a method for the clinical treatment of a plurality of malignant tumours, especially in solid form, in mammals by the administration of quinoline derivatives. Another objective is to provide structurally novel quinoline derivatives, having a pharmacological profile that is distinguished by high potency in experimental models and low level of side effects. The types of cancer that are especially inhibited by these quinoline derivatives include, for example, breast cancers, colon cancers, Kaposi's sarcoma, lung cancers, ovarian cancers, prostatic cancers, and skin cancers. More particularly, the present invention relates to quinoline derivatives suitable for the prevention of the development of malignant tumours, in particular prostatic cancers, and prevention and treatment of the metastases of malignant tumours, particularly of prostatic cancers. To increase the cure rate of metastatic malignant tumours, in particular of prostatic cancers, an effective therapy for malignant tumour cells, particularly androgen-independent prostatic cancer cells, is needed. The approach we have chosen is to inhibit the tumour-induced angiogenesis and to stimulate the host immune system to evoke/enhance an antitumour response. In the present invention, the ability of quinoline compounds to elicit an antitumour effect against an androgen-independent Dunning R-3327 AT-1 rat prostatic cancer was tested.

It has now surprisingly been found that the compounds of general formula (I)

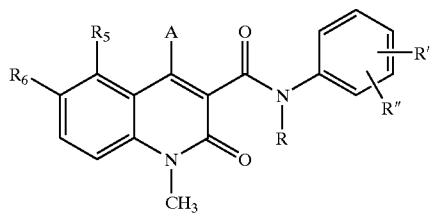

(I)

wherein
- A is selected from $OR_{41}$ and $NR_{42}R_{43}$ wherein
  - $R_{41}$ is selected from hydrogen and pharmaceutically acceptable inorganic cations, such as sodium, potassium and calcium, and organic cations such as monoethanolamine, diethanolamine, dimethylaminoethanol, morpholine and the like, and $COR_A$ wherein
  - $R_A$ is selected from alkyl and aryl groups, such as methyl, ethyl, n-propyl, iso-propyl, tert-butyl, neo-pentyl, phenyl, benzyl, phenethyl and the like;
  - $R_{42}$ and $R_{43}$ are the same and different and selected from hydrogen, methyl, ethyl, n-propyl, iso-propyl, n-butyl, cyclopropyl, cyclopentyl and cyclohexyl; or
  - $R_{42}$ is selected from benzyl and phenethyl, optionally mono- or disubstituted by a group selected from methyl, iso-propyl, methoxy, fluoro, chloro, bromo, dimethylamino, trifluoromethyl and nitro and $R_{43}$ is hydrogen; or
  - $R_{42}$ and $R_{43}$ together with the nitrogen to which they are bonded, form a 5- or 6'-membered ring; or
  - $R_{42}$ is $COR_B$ wherein
  - $R_B$ is selected from alkyl and aryl groups, such as C1–C4-alkyl, phenyl, benzyl and the like, or
  - from —$CH_2N(CH_3)_2$ and —$CH_1CH_2CH_2COOH$; or
  - $COR_B$ is a 2-acyloxymethylbenzoyl group

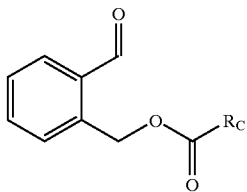

wherein
  - $R_C$ is selected from methyl, ethyl, phenyl and benzyl and the like; or
  - $R_{42}$ is $COOR_D$ wherein
  - $R_D$ is selected from C1–C4-alkyl, phenyl and benzyl; or
  - $R_{42}$ is —$CH_2OCO$-tert.-butyl; or
  - $R_{42}$ is $CONR_FR_G$ wherein
  - $R_F$ and $R_G$ are the same and different and are C1–C4-alkyl; or
  - $R_{42}$ is $CXNHR_E$ wherein
  - X is selected from O or S and $R_E$ is selected from C1–C4-alkyl, C2–C4-alkyl functionalised with an tertiary amino group, and phenyl, optionally functionalised with a p-chloro group; or
  - $R_{42}$ is $CH_2NR_HR_I$ wherein
  - $R_H$ and $R_I$ are the same and different and are C1–C4-alkyl or $R_H$ and $R_I$ together with the nitrogen to which they are bonded, form a morpholine ring; and
  - $R_{43}$ is selected from hydrogen, methyl, ethyl and cyclopropyl;
- R is selected from hydrogen, methyl, ethyl, n-propyl, iso-propyl, n-butyl, iso-butyl, sec.-butyl and allyl; with the proviso that R is not hydrogen when A is $OR_{41}$;
- R' is selected from hydrogen, methyl, methoxy, phenyl, fluoro, chloro, bromo, cyano, nitro, azido, trifluoromethyl, and $OCH_xF_y$,
  - wherein
  - x=0–2,
  - y=1–3 with the proviso that
  - x+y=3;

and with the proviso that R' is not hydrogen when R is methyl and A is $OR_{41}$;

- R" is selected from hydrogen, fluoro and chloro, with the proviso that R" is selected from fluoro and chloro only when R' is selected from fluoro and chloro;
- $R_5$ is selected from hydrogen, methyl, ethyl, n-propyl, iso-propyl, methoxy, ethoxy, thiomethyl, thioethyl, thio-n-propyl, thio-iso-propyl, fluoro, chloro, bromo, trifluoromethyl, nitro, amino, dimethylamino and $OCH_xF_y$, and $OCH_2CH_xF_y$,
  - wherein
  - x=0–2,
  - y=1–3 with the proviso that
  - x+y=3 and with the further provisos that $R_5$ is not fluoro or amino when A is $OR_{41}$; and that $R_5$ is hydrogen only when A is $NR_{42}R_{43}$ and R' is trifluoromethyl;

- $R_6$ is hydrogen; or
- $R_5$ and $R_6$ taken together are methylenedioxy;

are unexpectedly effective and specific in the treatment of individuals suffering from advanced cancer.

The compounds of general formula (I) may exist in different tautomeric forms and all such forms where such forms exist are included herein. Also optical isomers and racemates of the compounds of general formula (I) where such forms exist are included herein.

In a preferred embodiment of the invention $R_5$ is selected from methyl, ethyl, methoxy, ethoxy, thiomethyl, thioetyl, chloro, and bromo, or $R_5$ and $R_6$ taken together are methylenedioxy, A is selected from $OR_{41}$ and $NR_{42}R_{43}$, wherein $R_{41}$ is selected from hydrogen and sodium, and wherein $R_{42}$ and $R_{43}$ are the same and different and selected from hydrogen, methyl and ethyl, R is selected from hydrogen, methyl, ethyl and n-propyl, especially methyl and ethyl, and R' is selected from hydrogen, para-methyl, -phenyl, -methoxy, -chloro, -trifluoromethyl and -azido, especially from methoxy, chloro, and trifluoromethyl when R" is hydrogen, and R" is selected from meta'- and para-fluoro provided that R' is ortho-fluoro.

The invention also discloses novel compounds of the general formula (I')

(I')

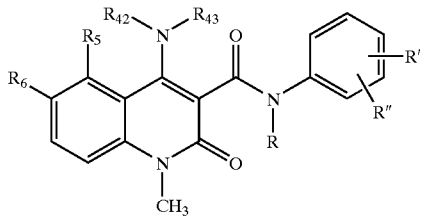

wherein
- $R_{42}$ and $R_{43}$ are the same and different and selected from hydrogen, methyl, ethyl, n-propyl, iso-propyl, n-butyl, cyclopropyl, cyclopentyl and cyclohexyl; or
- $R_{42}$ is selected from benzyl and phenethyl, optionally mono- or disubstituted by a group selected from methyl, iso-propyl, methoxy, fluoro, chloro, bromo, dimethylamino, trifluoromethyl and nitro and $R_{43}$ is hydrogen; or
- $R_{42}$ and $R_{43}$ together with the nitrogen to which they are bonded, form a 5- or 6-membered ring; or
- $R_{42}$ is $COR_B$ wherein
- $R_B$ is selected from alkyl and aryl groups, such as C1–C4-alkyl, phenyl, benzyl and the like; or
- from —$CH_2N(CH_3)_2$ and —$CH_2CH_2COOH$; or
- $COR_B$ is a 2-acyloxymethylbenzoyl group

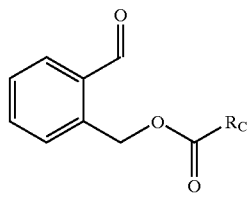

wherein
- $R_C$ is selected from methyl, ethyl, phenyl and benzyl and the like; or
- $R_{42}$ is $COOR_D$ wherein
- $R_D$ is selected from C1–C4-alkyl, phenyl and benzyl; or
- $R_{42}$ is —$CH_2OCO$-tert.-butyl; or
- $R_{42}$ is $CONR_FR_G$ wherein
- $R_F$ and $R_G$ are the same and different and are C1–C4-alkyl; or
- $R_{42}$ is $CXNHR_E$ wherein
- X is selected from O or S and $R_E$ is selected from C1–C4-alkyl, C2–C4-alkyl functionalised with an tertiary amino group, and phenyl, optionally functionalised with a p-chloro group; or
- $R_{42}$ is $CH_2NR_HR_I$ wherein
- $R_H$ and $R_I$ are the same and different and are C1–C4-alkyl or $R_H$ and $R_I$ together with the nitrogen to which they are bonded, form a morpholine ring; and
- $R_{43}$ is selected from hydrogen, methyl, ethyl and cyclopropyl;
- R is selected from hydrogen, methyl, ethyl, n-propyl, iso-propyl, n-butyl, iso-butyl, sec.-butyl and allyl;
- R' is selected from hydrogen, methyl, methoxy, fluoro, chloro, bromo, cyano, nitro, azido, trifluoromethyl, and $OCH_xF_y$, wherein
x=0–2,
y=1–3 with the proviso that
x+y=3,
- R" is selected from hydrogen, fluoro and chloro, with the proviso that R" is selected from fluoro and chloro only when R' is selected from fluoro and chloro;
- $R_5$ is selected from hydrogen, methyl, ethyl, n-propyl, iso-propyl, methoxy, ethoxy, thiomethyl, thioethyl, thio-n-propyl, thio-iso-propyl, fluoro, chloro, bromo, trifluoromethyl, nitro, amino, dimethylamino and $OCH_xF_y$, and $OCH_2CH_xF_y$ wherein
x=0–2,
y=1–3 with the proviso that
x+y=3 and
with the proviso that $R_5$ is hydrogen only when and R' is trifluoromethyl,
- $R_6$ is hydrogen; or
- $R_5$ and $R_6$ taken together are methylenedioxy;
or any tautomer, optical isomer or racemate thereof;
as well as novel compounds of the general formula (I")

(I")

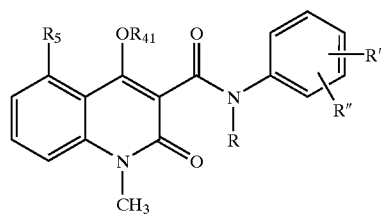

wherein
- R is selected from methyl, ethyl, n-propyl, iso-propyl, n-butyl, iso-butyl, sec.-butyl and allyl;
- $R_{41}$ is selected from hydrogen and pharmaceutically acceptable inorganic cations, such as sodium, potassium and calcium, and organic cations such as monoethanolamine, diethanolamine, dimethylaminoethanol, morpholine and the like; and $COR_A$ wherein
- $R_A$ is selected from alkyl and aryl groups, such as methyl, ethyl, n-propyl, iso-propyl, tert-butyl, neo-pentyl, phenyl, benzyl, phenethyl and the like;
- R' is selected from hydrogen and phenyl;
- R" is hydrogen;
- $R_5$ is methyl, ethyl, n-propyl, iso-propyl, methoxy, ethoxy, thiomethyl, thioethyl, thio-n-propyl, thio-iso-propyl, chloro, bromo, trifluoromethyl, dimethylamino and $OCH_xF_y$, and $OCH_2CH_xF_y$ wherein
x=0–2,
y=1–3 with the proviso that
x+y=3 and;
with the further proviso that R' only is hydrogen when $R_5$ is dimethylamino and R is different from methyl,
or any tautomer, optical isomer or racemate thereof.

Among the most preferred compounds are: N-ethyl-N-phenyl-1,2-dihydro-4-hydroxy-1,5-dimethyl-2-oxo-quinoline-3-carboxamide, N-ethyl-N-phenyl-1,2-dihydro-4-hydroxy-5-ethyl-1-methyl-2-oxo-quinoline-3-carboxamide, N-ethyl-N-phenyl-1,2-dihydro-4-hydroxy-5-methoxy-1- methyl-2-oxo-quinoline-3-carboxamide, N-ethyl-N-phenyl-1,2-dihydro-4-hydroxy-5-chloro-1-methyl-2-oxo-quinoline-3-carboxamide or its sodium salt, N-ethyl-N-phenyl-1,2-dihydro-4-hydroxy-5-bromo-1-methyl-2-oxo-quinoline-3-carboxamide, N-ethyl-N-phenyl-1,2-dihydro-4-hydroxy-5,6-methylenedioxy-1-methyl-2-oxo-quinoline-3-carboxamide, N-ethyl-N-phenyl-1,2-dihydro-4-hydroxy-5-dimethylamino-1-methyl-2-oxo-quinoline-3-carboxamide, N-ethyl-N-(3-fluoro-phenyl)-1,2-dihydro-4-hydroxy-5-chloro-1-methyl-2-oxo-quinoline-3-carboxamide, N-methyl-N-(4-chloro-phenyl)-1,2-dihydro-4-hydroxy-5-chloro-1-methyl-2-oxo-quinoline-3-carboxamide, N-methyl-N-(4-methyl-phenyl)-1,2-dihydro-4-hydroxy-5-chloro-1-methyl-2-oxo-quinoline-3-carboxamide, N-methyl-N-(4-phenyl-phenyl)-1,2-dihydro-4-hydroxy-5-chloro-1-methyl-2-oxo-quinoline-3-carboxamide, N-methyl-N-(2,4-difluoro-phenyl)-1,2-dihydro-4-hydroxy-5-chloro-1-methyl-2-oxo-quinoline-3-carboxamide, N-methyl-N-(2,5-difluoro-phenyl)-1,2-dihydro-4-hydroxy-5-chloro-1-methyl-2-oxo-quinoline-3-carboxamide, N-ethyl-N-(3-methoxy-phenyl)-1,2-dihydro-4-hydroxy-5-ethyl-1-methyl-2-oxo-quinoline-3-carboxamide, N-methyl-N-(2,4-difluoro-phenyl)-1,2-dihydro-4-hydroxy-5-methoxy-1-methyl-2-oxo-quinoline-3-carboxamide, N-methyl-N-(2,5-difluoro-phenyl)-1,2-dihydro-4-hydroxy-5-methoxy-1-methyl-2-oxo-quinoline-3-carboxamide, N-methyl-N-(4-trifluoromethyl-phenyl)-1,2-dihydro-4-hydroxy-5-methoxy-1-methyl-2-oxo-quinoline-3-carboxamide, N-methyl-N-(2,4-difluoro-phenyl)-1,2-dihydro-4-hydroxy-5,6-methylenedioxy-1-methyl-2-oxo-quinoline-3-carboxamide, N-methyl-N-(4-chloro-phenyl)-1,2-dihydro-4-hydroxy-1,5-dimethyl-2-oxo-quinoline-3-carboxamide, N-methyl-N-(2,4-difluoro-phenyl)-1,2-dihydro-4-hydroxy-5-ethyl-1-methyl-2-oxo-quinoline-3-carboxamide, N-n-propyl-N-phenyl-1,2-dihydro-4-hydroxy-5-thiomethyl-1-methyl-2-oxo-quinoline-3-carboxamide, N-methyl-N-(4-chloro-phenyl)-1,2-dihydro-4-hydroxy-5-thiomethyl-1-methyl-2-oxo-quinoline-3-carboxamide, N-methyl-N-(4-trifluoromethyl-phenyl)-1,2-dihydro-4-hydroxy-5-thiomethyl-1-methyl-2-oxo-quinoline-3-carboxamide, N-methyl-N-(2,4-difluoro-phenyl)-1,2-dihydro-4-hydroxy-5-thiomethyl-1-methyl-2-oxo-quinoline-3-carboxamide, N-methyl-N-(2,5-difluoro-phenyl)-1,2-dihydro-4-hydroxy-5-thiomethyl-1-methyl-2-oxo-quinoline-3-carboxamide, N-methyl-N-(4-methoxy-phenyl)-1,2-dihydro-5-dimethylamino-4-hydroxy-1-methyl-2-oxo-quinoline-3-carboxyde, N-methyl-N-phenyl-4-amino-1,2-dihydro-1,5-dimethyl-2-oxo-quinoline-3-carboxamide, N-methyl-N-phenyl-4-amino-1,2-dihydro-5-methoxy-1-methyl-2-oxo-quinoline-3-carboxamide, N-methyl-N-phenyl-5-chloro-1,2-dihydro-4-(N-methylamino)-1-methyl-2-oxo-quinoline-3-carboxamide, N-methyl-N-phenyl-1,2-dihydro-1,5-dimethyl-4-(N-methylamino)-2-oxo-quinoline-3-carboxamide, N-methyl-N-phenyl-1,2-dihydro-5-methoxy-4-(N-methylamino)-1-methyl-2-oxo-quinoline-3-carboxamide, N-methyl-N-(4-trifluoromethyl-phenyl)-4-amino-1,2-dihydro-1-methyl-2-oxo-quinoline-3-carboxamide.

High crystal lattice energy of solid compounds results in poor solubility, e.g., in water. Hence, an approach to reduce this energy will result in improved aqueous solubility. The prodrug per se is an inactive species. A basal requisite for a prodrug approach is the reconversion of the prodrug to the parent drug in vivo. The prodrug—drug conversion may take place before, during or after absorption. The necessary conversion of prodrugs to the parent drug molecules in the body can take place by a variety of reactions. The most common prodrugs are those requiring a hydrolytic cleavage mediated by enzymatic hydrolysis. In other cases, drug molecules are regenerated from their prodrugs by biochemical reductive or oxidative processes.

Esters of drugs containing a hydroxyl function have been considered as prodrug types primarily from the fact that the organism is rich in enzymes capable of hydrolysing esters.

Compounds of the present invention contain an enolised carbonyl group as a prominent functional group. Under proper conditions, the enol form can be trapped by acylation of the enol group. Steric and electronic effects within the acyl group have a substantial influence upon both the aqueous and enzymatic rates of hydrolysis. Besides, physicochemical properties such as water-solubility, lipophilicity and dissolution rate can be modified for the parent compound.

Compounds of the present invention contain a 4-amino function. N-Acylation of amines to give activated amides may be a promising means of obtaining prodrug forms. 2-Hydroxymethylbenzamides undergo a cyclisation (lactonisation) in aqueous solution to give phtalide and free amine. Substitution of the two methylene hydrogen atoms of 2-hydroxymethylbenzamide with, for example, methyl and phenyl groups greatly affects the lactonisation rates. Also blocking the lactonisation by acylation of the 2-hydroxymethylbenzamides to give 2-acyloxymethylbenzamides affects the lactonization that must be preceded by hydrolysis of the ester grouping. Furthermore, the acylation allows control of the lipophilicity/hydrophilicity of the prodrug by the appropriate selection of the acyl group. The use of various carbamate derivatives as well as N-Mannich bases can also be considered as means to forming prodrugs.

The compounds of general formula (I) were assayed for their capacity to inhibit of growth of the Dunning R-3327 AT-1 tumour, a prostatic rat cancer. Roquinimex was used as positive treatment control and showed a 30% inhibition at 4 mg/kg.

The compounds of general formula (I) wherein A is $NR_{42}R_{43}$ are prepared by the following method:

Method A

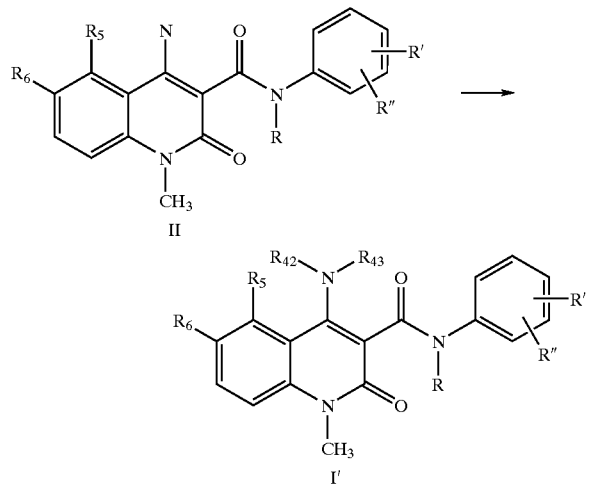

The compounds of formula (I') may be prepared by known methods, for example, by reaction of 4-chloro-1,2-dihydro-2-oxo-quinoline-3-carboxamide derivative (X=Cl; II) known from U.S. Pat. No. 4,547,511 with an amino compound in a suitable solvent such as an alcohol, e.g., ethanol. All compounds had satisfactory $^1$H-NMR and mass spectra, although the NMR spectra were complicated due to presence of E and Z amide isomers. Only the major isomer is described by NMR-shifts below.
Method B

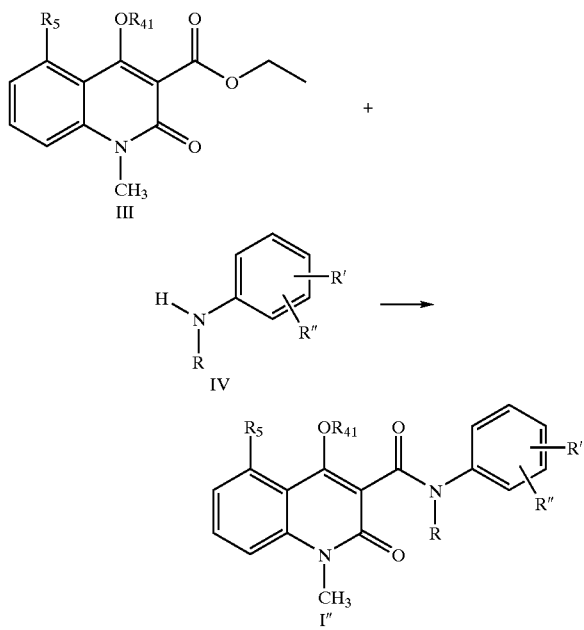

The compounds of general formula (I") may be prepared by methods known from U.S. Pat. No. 6,077,851 and, for example, as shown above, by reaction of an ester derivative of the quinoline carboxylic acid with an aniline in a suitable solvent such as toluene, xylene and the like. General methods for preparation of the quinoline carboxylic acid ester derivatives of formula (III) are known from U.S. Pat. No. 4,547,511. N-alkylated anilines of formula (IV) are commercially available or known from literature, e.g., in Johnstone et al, J. Chem. Soc. 1969, 2223–2224. Compounds falling within the scope of formula (IV) may be prepared by methods, which are generally analogous to those of said literature.

The scope of the invention is as defined in the claims, which hereby are included by reference.

The following examples are intended to illustrate the invention without restricting the scope thereof.

EXAMPLE 1

N-Methyl-N-phenyl-4-chloro-1,2-dihydro-1,5-dimethyl-2-oxo-quinoline-3-carboxamide N-methyl-N-phenyl-1,2-dihydro-4-hydroxy-1,5-dimethyl-2-oxo-quinoline-3-carboxamide (3.5 g) was heated in phosphorus oxytrichloride (7 ml) at 100° C. for 2 hours. The mixture was concentrated, dissolved in dichloromethane and washed with water. The organic phase was dried ($Na_2SO_4$) and concentrated. The residue was triturated with ethyl acetate and filtered to give the title compound (2.3 g).

$^1$H NMR ($CDCl_3$): δ7.50–7.00 (8H, aromatic protons), 3.60 (N—Me, s), 3.48 (N—Me, s), 2.80 (PhMe, s).

Mass (ESI, m/z) [M+H]$^+$: 341.

In essentially the same manner the following compounds were obtained from the corresponding starting materials:

N-methyl-N-phenyl-4,5-dichloro-1,2-dihydro-1-methyl-2-oxo-quinoline-3-carboxamide $^1$H NMR ($CDCl_3$+TFA): δ7.55–7.15 (8H, aromatic protons), 3.60 (N—Me, s), 3.47 (N—Me, s).

Mass (ESI, m/z) [M+H]$^+$: 361.

N-methyl-N-(4-trifluoromethyl-phenyl)-4-chloro-1,2-dihydro-1-methyl-2-oxo-quinoline-3-carboxamide $^1$H NMR ($CDCl_3$): δ8.10–7.22 (8H, aromatic protons), 3.60 (N—Me, s), 3.47 (N—Me, s).

Mass (ESI, m/z) [M+H]$^+$: 395.

EXAMPLE 2

N-methyl-N-phenyl-1,2-dihydro-4-(N,N-dimethylamino)-1,5-dimethyl-2-oxo-quinoline-3-carboxamide N-Methyl-N-phenyl-4-chloro-1,2-dihydro-1,5-dimethyl-2-oxo-quinoline-3-carboxamide (0.52 g) in a mixture of dimethylamine and ethanol was heated in a thick-walled glass flask stoppered by a screw cap. The reaction was monitored by TLC (mixtures of dichloromethane/methanol were used as elutents). After 8 hours of heating the flask was cooled, opened, and diluted with water. The resulting precipitate was filtered, washed with water and dried in vacuum to afford the title compound (0.39 g).

$^1$H NMR ($CDCl_3$+TFA): δ7.50–6.70 (8H, aromatic protons), 3.70 (N—Me, s), 3.58 (N—Me, s), 3.50 (N—Me, s), 3.43 (N—Me, s).

Mass (ESI, m/z) [M+H]$^+$: found 350, expected 350.

In essentially the same manner the following compounds were obtained from the corresponding starting materials:

N-methyl-N-phenyl-1,2-dihydro-1,5-dimethyl-4-(N-methylamino)-2-oxo-quinoline-3-carboxamide $^1$H NMR ($CDCl_3$+TFA): δ7.80–6.80 (8H, aromatic protons), 3.82 (N—Me, s), 3.59 (N—Me, s), 3.10 (N—Me, s), 1.85 (PhMe, s).

Mass (ESI, m/z) [M+H]$^+$: 336

N-methyl-N-phenyl-4-amino-1,2-dihydro-1,5-dimethyl-2-oxo-quinoline-3-carboxamide $^1$H NMR ($CDCl_3$+TFA): δ7.80–6.40 (8H, aromatic protons), 3.80 (N—Me, s), 3.57 (N—Me, s), 2.28 (PhMe, s).

Mass (ESI, m/z) [M+H]$^+$: 322

N-methyl-N-phenyl-5-chloro-1,2-dihydro-4-(N,N-dimethylamino)-1-methyl-2-oxo-quinoline-3-carboxamide $^1$H NMR ($CDCl_3$+TFA): δ7.70–7.00 (8H, aromatic protons), 3.68 (N—Me, s), 3.50 (N—Me, s), 3.18 N—$Me_2$, s).

Mass (ESI, m/z) [M+H]$^+$: 370

N-methyl-N-phenyl-5-chloro-1,2-dihydro-4-(N-methylamino)-1-methyl-2-oxo-quinoline-3-carboxamide $^1$H NMR ($CDCl_3$+TFA): δ7.60–7.00 (8H, aromatic protons), 3.73 (N—Me, s), 3.57 (N—Me, s), 3.15 (N—Me, s).

Mass (ESI, m/z) [M+H]$^+$: 356.

N-methyl-N-phenyl-4-amino-5-chloro-1,2-dihydro-1-methyl-2-oxo-quinoline-3-carboxamide $^1$H NMR ($CDCl_3$+TFA): δ7.62–7.23 (8H, aromatic protons), 3.63 (N—Me, s), 3.50 (N—Me, s).

Mass (ESI, m/z) [M+H]$^+$: 342.

N-ethyl-N-phenyl-5-bromo-1,2-dihydro-4-(N-ethylamino)-1-methyl-2-oxo-quinoline-3-carboxamide, N-ethyl-N-phenyl-5-chloro-4-(N-cyclopentylamino)-1,2-dihydro-1-methyl-2-oxo-quinoline-3-carboxamide, N-ethyl-N-phenyl-5-chloro-1,2-dihydro-4-(N-methylamino)-1-methyl-2-oxo-quinoline-3-carboxamide, N-ethyl-N-phenyl-1,2-dihydro-5-ethyl-4-(N-ethylamino)-1-methyl-2-oxo-quinoline-3-carboxamide N-ethyl-N-phenyl-1,2-dihydro-4-(N,N-dimethylamino)-5-methoxy-1-methyl-2-oxo-quinoline-3-carboxamide, N-ethyl-N-phenyl-4-(N,N-diethylamino)-1,2-dihydro-1-methyl-5-trifluoromethyl-2-oxo-quinoline-3-carboxamide, N-methyl-N-phenyl-1,2-dihydro-5-fluoro-1-methyl-4-(1-pyrrolidinyl)-2-oxo-quinoline-3-carboxamide, N-methyl-N-phenyl-1,2-dihydro-5-ethyl-1-methyl-4-(1-piperidinyl)-2-oxo-quinoline-3-carboxamide, N-methyl-N-phenyl-1,2-dihydro-1,5-dimethyl-4-(N-ethylamino)-2-oxo-quinoline-3-carboxamide, N-methyl-N-phenyl-1,2-dihydro-4-(N,N-dimethylamino)-5-methoxy-1-methyl-2-oxo-quinoline-3-carboxamide, N-methyl-N-phenyl-4-(N-benzylamino)-1,2-dihydro-5-methoxy-1-methyl-2-oxo-quinoline-3-carboxamide, N-methyl-N-phenyl-1,2-dihydro-5-methoxy-1-methyl-4-(N-methylamino)-2-oxo-quinoline-3-carboxamide, N-methyl-N-phenyl-1,2-dihydro-4-(N,N-dimethylamino)-1-methyl-5-trifluoromethyl-2 -oxo-quinoline-3-carboxamide, N-methyl-N-phenyl-4-[(4-chlorophenyl)amino]-1,2-dihydro-1-methyl-5-trifluoromethyl-2-oxo-quinoline-3-carboxamide, N-(n-propyl)-N-phenyl-5-chloro-1,2-dihydro-4-(N-methylamino)-1-methyl-2-oxo-quinoline-3-carboxamide, N-iso-propyl-N-phenyl-1,2-dihydro-5-ethyl-4-(N-ethylamino)-1-methyl-2-oxo-quinoline-3-carboxamide.

The following two 4-amino derivatives were prepared by a slight modification of the method described above. After cooling, the reaction mixture was concentrated and dissolved in dichloromethane. The organic phase was extracted with water, dried and concentrated to furnish the product.

N-methyl-N-(4-trifluoromethyl-phenyl)-1,2-dihydro-1-methyl-4-(N-methylamino)-2-oxo-quinoline-3-carboxamide $^1$H NMR (CDCl$_3$+TFA): δ7.82–7.24 (8H, aromatic protons), 3.85 (N—Me, s), 3.52 (N—Me, 3.18 (N—Me, s).

Mass (ESI, m/z) [M+H]$^+$: 390.

N-methyl-N-(4-trifluoromethyl-phenyl)-1,2-dihydro-4-(N,N-dimethylamino)-1-methyl-2-oxo-quinoline-3-carboxamide $^1$H NMR (CDCl$_3$+TFA): δ7.80–6.87 (8H, aromatic protons), 3.78 (N—Me, s), 3.58 (N—Me, s), 3.25 (N—Me$_2$, s).

Mass (ESI, m/z) [M+H]$^+$: 404.

EXAMPLE 3

1,2-Dihydro-4-hydroxy-5-dimethylamino-1-methyl-2-oxo-quinoline-3-carboxylic acid ethyl ester A solution of 2,6-difluorobensonitrile (35.7 g, 0.26 mol) and dimethylamine (17.5 g, 0.39 mol) in 100 ml of anhydrous isopropanol was heated at 110° C. for 18 hours in an autoclave. After cooling, the solvent was evaporated and the residue worked up with water and diethyl ether to give a yellowish oil of 2-dimethylamino-6-fluorobensonitrile (41 g) contaminated with 2–4% of 2,6-di(dimethylamino) bensonitrile. This crude mixture was solved in 40% aqueous methylamine (130 ml, 1.5 mol) and ethanol (100 ml) and heated at 110° C. for 18 hours in an autoclave. The product was worked up as above to give 44 g of 2-dimethylamino-6-methylaminobensonitrile (>95% pure). This was hydrolysed in conc. sulphuric acid (170 ml) and water (34 ml) at 120° C. for 3 hours. The brown solution was cooled and neutralised with 5 M NaOH. The resulting cloudy mixture was filtered through celite and washed with 30 ml of diethyl ether. The aqueous solution was extracted with dichloromethane (3×50 ml), the extracts were washed with water and evaporated to give 6-dimethylamino-N-methyl-anthranilic acid. The anthranilic acid (21.5 g, 0.11 mol) was dissolved in 250 ml of 1,4-dioxane. Phosgene (25 ml, 0.45 mol) was slowly added under cooling in an ice bath. The mixture was warmed at 40° C. for 1 hour, cooled to 15° C., and the product was collected by filtration. This was worked up with aqueous sodium bicarbonate and dichloromethane, the organ phase carefully dried and evaporated to give pure 5-dimethylamino-N-methyl-isatoic anhydride. The anhydride (22 g, 0.10 mol) was dissolved in anhydrous methanol (150 ml) and sodium methoxide (5.4 g, 0.10 mol) was added. After stirring at 50° C. for 3 hours, the solvent was removed and the residue worked up with water and ether to give a yellow oil (15 g). The oil, 6-dimethylamino-N-methyl-anthranilic acid methyl ester (10.4 g, 0.05 mol), was dissolved in dichloromethane (100 ml) and cooled on an ice-bath. Ethyl malonyl chloride (10 g, 0.07 mol) was added. After being stirred for 1 hour at room temperature the cloudy mixture was washed with aqueous sodium bicarbonate. The organic phase was carefully dried and concentrated under vacuum. The residue was dissolved in dry ethanol (100 ml) and sodium methoxide (9 g, 0.16 mol) was added. The mixture was stirred for 1 hour and neutralised with hydrochloric acid. The solvent was removed and the residue worked up with water and dichloromethane. The organic phase was dried and the solvent removed to give the title compound as pure, greyish crystals (11 g).

$^1$H NMR (CDCl3) δ1.36 (3H, t), 2.78 (6H, s), 3.59 (3H, s), 4.39 (2H, q), 7.17 (1H, d), 7.21 (1H, d), 7.54 (1H, t), 17.1 (1H, s).

EXAMPLE 4

N-Ethyl-N-phenyl-1,2-dihydro-5-dimethylamino-4-hydroxy-1-methyl-2-oxo-quinoline-3-carboxamide
(Method B)

N-Ethylaniline (4.4 g, 0.036 mol) was dissolved in 80 ml of toluene. About 30 ml of the solvent was distilled off in order to obtain a dry solution. 1,2-Dihydro-4-hydroxy-5-dimethylamino-1-methyl-2-oxo-quinoline-3-carboxylic acid ethyl ester (3.5 g, 0.012 mol) was added to the boiling solution. The ethanol formed during the reaction was distilled off together with some toluene for about 10 hours. The mixture was cooled to room temperature. The precipitate was collected, washed with cold toluene and hexane and dried to give the title compound (3.1 g), yield 71%.

$^1$H NMR (CDCl3) δ1.25 (3H, t), 2.63 (3H, s), 2.78 (3H, s), 3.51 (3H, s), 3.87–4.07 (2H, m), 7.07–7.19 (5H, m), 7.39–7.48 (3H, m).

$^{13}$C NMR (CDCl3) δ13.2 (CH3), 29.4 (CH3), 43.7 (CH2), 45.2 (CH3), 46.5 (CH3), 109.6 (C), 110.4 (C), 113.0 (CH), 114.0 (CH), 127.3 (CH), 127.5+127.5 (CH), 128.3+128.3 (CH), 130.8 (CH), 140.7 (C), 142.3 (C), 150.6 (C), 159.7 (C), 160.6 (C=O), 165.0 (C=O).

Mass (ESI m/z) [M+H]$^+$366, fragment 245.

EXAMPLE 5

N-Metyl-4-aminodiphenyl

To a cooled solution of 4-bromoaniline (3.4 g, 0.02 mol) and triethylamine (5.5 ml, 0.04 mol) in dichloromethane (50 ml) was slowly added trifluoroacetic anhydride (3.4 ml, 0.024 mol). After 1 hour stirring, the mixture was worked up with aqueous hydrochloric acid (0.5 M) and aqueous sodium bicarbonate. The organic phase was dried and evaporated to dryness. The crystals (5.2 g) formed was dissolved in dry tetrahydrofuran (40 ml), cooled and treated with potassium tert.-butoxide (3.4 g, 0.03 mol). After 1 hour stirring, methyl iodide (3.8 ml, 0.06 mol) was added and the mixture left overnight. The mixture was worked up in the usual manner with aqueous hydrochloric acid (0.5 M), aqueous sodium bicarbonate, dried and evaporated to dryness to give 4.6 g of the intermediate N-(4-bromophenyl)-2,2,2-trifluoro-N-methylacetamide. In a Suzuki cross-coupling reaction, this material (4.6 g, 0.016 mol) was charged in a carefully nitrogen purged reaction-vessel along with toluene (40 ml), sodium bicarbonate (5.4 g, 0.064 mol), tetrakis (triphenylphosphine)palladium(0) (0.6 g, 0.048 mol) and water (15 ml). Benseneboronic acid (2.2 g, 0.017 mol) dissolved in ethanol (8 ml) was added into the vessel and the black mixture was heated to reflux under strong stirring during 10 hours. The mixture was cooled, filtered through celite and the organic phase evaporated to dryness. The residue was recrystallised from ethanol to give beige crystals ( 2.4 g, 54 % yield). The crystals were hydrolysed in a methanol/ammonia 1:1 mixture (50 ml) under short heating, (1 hour). The solvents were evaporated and the residue dissolved in dichloromethane (25 ml), dried and evaporated to dryness to give the title compound as 1.3 g syrup.

$^1$H NMR (CDCl3) $\delta$2.88 (3H, s), 6.70 (2H, d), 7.27 (1H, t), 7.41 (2H, t), 7.48 (2H, d), 7.57 (2H, d).

EXAMPLE 6

N-(4-phenyl-phenyl)-N-methyl-5-chloro-1,2-dihydro-4-hydroxy-1-methyl-2-oxo-quinoline-3-carboxamide To an ice-cold solution of 5-chloro-1,2-dihydro-4-hydroxy-1-methyl-2-oxo-quinoline-3-carboxylic acid (1.6 g, 6.5 mmol), triethylamine (3 ml, 22.7 mmols), N-metyl-4-aminodiphenyl (1.3 g, 7 mmol) in methylene chloride (25 ml) was added dropwise during 10 minutes a solution of thionyl chloride (1.0 g, 8.4 mmol) in methylene chloride (10 ml). Stirring was continued at 4° C. for 4 hours. The solution was diluted with methylene chloride (10 ml), washed with cold 1 M sulphuric acid and then extracted with 1 M sodium hydroxide. The pH of the aqueous phase was adjusted to 8–8.5, clarified by filtration and then further acidified with hydrochloric acid solution to pH 4. After standing a crystalline precipitate was formed and was filtered off, washed with water and dried to give the title compound (1.9 g).

$^1$H NMR (CDCl3) $\delta$3.33 (3H, s), 3.52 (3H, s), 7.13 (1H, d), 7.20–7.35 (4H, m), 7.36–7.56 (7H, m).

All embodiments of the invention as disclosed in the claims are herewith included in the specification.

Pharmacological Methods

Primary Screen

R-3327 AT-1 Prostatic cancer in man is an angiogenic type of solid tumour. The Dunning R-3327 AT-1 is a prostatic cancer of the rat and suits as an experimental animal model for this disease. The AT-1 tumour is serially transplanted subcutaneously (sc) on syngeneic rats of the Copenhagen strain. Small pieces of the tumour are transplanted sc to recipient rats and treatment of the tumour bearing rats start when the tumours are easily measurable approximately on day 10 after transplantation. Doses of the compounds are given either orally or parentally 5 days a week for four weeks. The tumour growth and body weight gain are monitored during the experimental time.

Assays for Evaluation of Pro-inflammatory Activity

Beagle Pain Syndrome

The Beagle Pain Syndrome (BPS) is reflected by clinical and laboratory manifestations, e.g., fever, increased erythrocyte sedimentation rate (ESR), alkaline phosphate (AP), induction of acute phase proteins and vasculitis, justifying BPS as a model for the flu-like syndrome induced by roquinimex in man. BPS is a disease of acute inflammatory nature. Several alterations in hematology and clinical chemistry are occurring. The compounds were administrated intravenously to beagle dogs. The dosage was given for five consecutive days. The dogs were evaluated for a pro-inflammatory reaction, i.e., increased ESR and AP. The percentage change of the laboratory values between Day 8 and baseline was determined.

Neutrophil Inflammation

Neutrophil inflammation (NI) is induced by intradermal injection of carrageenin or zymosan. Accumulation of neutrophils is evaluated by measuring the neutrophil enzyme myeloperoxidase activity from challenged skin.

Oedema Formation

Oedema formation is induced by intradermal injection of carrageenin. The extent of oedema is evaluated by measuring the plasma extravasation of intravenously injected Evans blue in challenged skin.

Delayed Type Hypersensitivity

Delayed Type Hypersensitivity (DTH) reactions are T-cell mediated and antigen-specific inflammatory reactions useful for studies on modulation of immunological and inflammatory events. Mice are sensitised to oxazolone by cutaneous administration. Challenge is performed topically on the ears and the inflammatory reaction is quantified by measuring change in ear thickness.

The following examples are intended to illustrate the invention without restricting the scope thereof Among preferred compounds are N-ethyl-N-phenyl-1,2-dihydro-4-hydroxy-5-chloro-1-methyl-2-oxo-quinoline-3-carboxamide, N-methyl-N-(4-chloro-phenyl)-1,2-dihydro-4-hydroxy-5-chloro-1-methyl-2-oxo-quinoline-3-carboxamide, N-methyl-N-(2,4-difluoro-phenyl)-1,2-dihydro-4-hydroxy-5-thiomethyl-1-methyl-2-oxo-quinoline-3-carboxamide and N-methyl-N-phenyl-4-amino-1,2-dihydro-1,5-dimethyl-2-oxo-quinoline-3-carboxamide hereinafter-called Compound A, B, C and D, respectively. Roquinimex is included as a reference compound hereinafter called Compound E. In addition, the antineoplastic agents vinblastine (Merck Index $12^{th}$ Ed., No. 10119) and doxorubicin (Merck Index $12^{th}$ Ed., No. 3495) have been included as reference compounds.

| Tumour growth inhibition | | |
|---|---|---|
| Compound | Dose (mg/kg) | % Tumour Weight Reduction |
| A (invention) | 2 (sc) | 37 |
| B (invention) | 2 (po) | 28 |
| C (invention) | 2 (po) | 39 |
| D (invention) | 2 (sc) | 38 |
| E (reference) | 4 (sc) | 30 |
| vinblastine (reference) | 1 (iv)[a] | 0 |
| vinblastine (reference) | 4 (iv)[a] | toxic |
| doxorubicin (reference) | 4 (ip)[a] | 0 |
| doxorubicin (reference) | 8 (ip)[a] | 31[b] |

[a] treatment given on Day 11
[b] 8 mg/kg of doxorubicin caused a body weight loss

| Beagle Pain Syndrome - percentage change (Day 8 - baseline) | | | | |
|---|---|---|---|---|
| | Compound A (invention) | | Compound E (reference) | |
| Dose, mg/kg p. o. | ESR | AP | ESR | AP |
| 1 | 177 | 25 | 700 | 103 |
| 10 | 515 | 109 | | |

The administration of compounds of formula I in order to practice the present methods of therapy is carried out by administering an effective amount of the chosen compound to the patient in need of such treatment or prophylaxis. The effective amount of an individual compound is determined by a physician and depends on factors such as the exact disease to be treated, the severity of the disease and other diseases or conditions from which the patient suffers, and other factors in tile physician's judgement. It will be observed that the compounds are active at low dosage levels, thereby allowing effective treatment or prophylaxes with slight probability of side effects or cross-reactions with other treatments or drugs. A suitable daily dose for use in the treatment of the disease is contemplated to vary between 0.002 mg/kg to about 100 mg/kg body weight, in particular between 0.02 mg/kg to 10 mg/kg body weight, depending upon the specific condition, e.g., prostatic cancer, to be treated, the age and weight of the specific patient, and the specific patient's response to the medication. The exact individual dosage, as well as the daily dosage, will be determined according to standard medical principles under the direction of a physician.

Effective quantities of the compounds of formula (I) are preferably administered to a patient in need of such treatment according to usual routes of administration and formulated in usual pharmaceutical compositions comprising an effective amount of the active ingredient and a suitable pharmaceutically acceptable carrier. By "pharmaceutically acceptable" it is meant the carrier, diluent or excipient must be compatible with the other ingredients of the formulation and not deleterious to the recipient thereof Such compositions may take a variety of forms, e.g. solutions, suspensions, emulsions, tablets, capsules, and powders prepared for oral administration, sterile solutions for parental administration, suppositories for rectal administration or suitable topical formulations. In making the composition of the present invention, the active ingredient will usually be admixed with a carrier, or diluted by a carrier, or enclosed within a carrier that may be in the form of a capsule, sachet, paper, or other container. When the carrier serves as a diluent, it may be a solid, semi-solid or liquid material that acts as a vehicle, excipient or medium for the active ingredient. Various additives to enhance the stability or ease of administration of the drug are contemplated. Thus, the compositions can be in the form of tablets, pills, powders, lozenges, sachets, cachets, elixirs, suspensions, emulsions solutions, syrups, aerosols (as a solid or in a liquid medium), soft and hard gelatine capsules, suppositories, sterile injectable solutions, sterile packaged powders, and the like. Conventional procedures for the selection and preparation of suitable pharmaceutical formulations are described, for example, in "Pharmaceuticals—The Science of Dosage Form Design", M. B. Aulton, Churchill Livingstone, 1988. The pharmaceutical composition may also contain additional therapeutically useful substances other than a compound of formula (I).

REFERENCE

1. Ichikawa, T. et al., The antitumor effects of the quinoline-3-carboxamide Linomide on Dunning R-3327 rat prostatic cancers. Cancer Research 52:3022–3028, 1992.
2. de Wit, R,. et al., EORTC phase II study of daily oral linomide in metastatic renal cell carcinoma patients with good prognostic factors. Eur. J. Cancer 33:493–495, 1997.
3. Kelly, D. F., Grimsell, C. S. G. and Kenyon, C. J., Polyarteritis in the dog: A case report. Vet Record 92: 363–366, 1973.
4. Harcourt, R. A., Polyarterites in a colony of beagles. Vet Record 102: 519–522, 1978.

We claim:

1. A method for the treatment of breast or prostrate cancers in a mammal comprising administration to said mammal of an amount effective therefor of a compound of the formula (I)

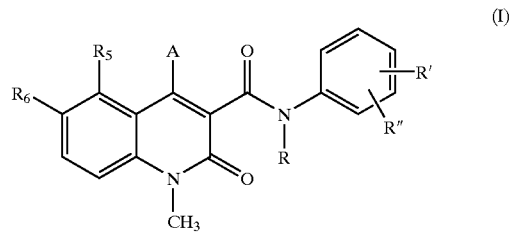

(I)

wherein
A is selected from the group consisting of $OR_{41}$ and $NR_{42}R_{43}$ wherein
$R_{41}$ is selected from the group consisting of hydrogen and pharmaceutically acceptable inorganic cations, and organic cations; and $COR_A$ wherein
$R_A$ is selected from the group consisting of alkyl and aryl groups;
$R_{42}$ and $R_{43}$ are the same and different and selected from the group consisting of hydrogen, methyl, ethyl, n-propyl, iso-propyl, and cyclopropyl, or
$R_{42}$ is $COR_B$ wherein
$R_B$ is selected from C1–C4-alkyl, or
$COR_B$ is a 2-acyloxymethylbenzoyl group

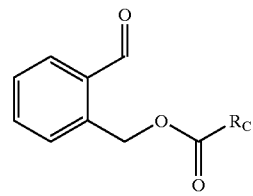

wherein
$R_C$ is selected from the group consisting of methyl, ethyl, phenyl and benzyl;
$R_{43}$ is as defined above;
R is selected from the group consisting of hydrogen, methyl, ethyl, n-propyl, iso-propyl, n-butyl, iso-butyl, sec.-butyl and allyl; with the proviso that R is not hydrogen when A is $OR_{41}$;
R' is selected from the group consisting of hydrogen, methyl, methoxy, fluoro, chloro, bromo, cyano, trifluoromethyl, and $OCH_xF_y$,
wherein
x=0–2,
y=1–3 with the provisos that
x+y=3;

and that R' is not hydrogen when R is methyl and A is $OR_{41}$;

R" is selected from the group consisting of hydrogen, fluoro and chloro, with the proviso that R" is selected from fluoro and chloro only when R' is selected from fluoro and chloro;

$R_5$ is selected from the group consisting of hydrogen, methyl, ethyl, n-propyl, iso-propyl, methoxy, ethoxy, fluoro, chloro, bromo, dimethylamino $OCH_xF_y$, and $OCH_2CH_xF_y$
wherein
x=0–2,
y=1–3 with the provisos that
x+y=3 and
that $R_5$ is not fluoro when A is $OR_{41}$; and that $R_5$ is hydrogen only when A is $NR_{42}R_{43}$ and R' is trifluoromethyl;

$R_6$ is hydrogen; or $R_5$ and $R_6$ taken together are methylenedioxy;
or any tautomer thereof.

2. The method according to claim 1, comprising the administration of compounds wherein A is $OR_{41}$.

3. The method according to claim 1, comprising the administration of compounds wherein A is $NR_{42}R_{43}$.

4. The method according to claim 2, comprising the administration of compounds wherein $R_5$ is methyl, ethyl, methoxy, chloro, bromo, and $R_5$ and $R_6$ taken together are methylenedioxy.

5. The method according to claim 4, comprising the administration of compounds wherein R is methyl and ethyl.

6. The method according to claim 5, comprising the administration of compounds wherein R is ethyl and R' is hydrogen.

7. The method according to claim 4, comprising the administration of compounds wherein R' is selected from the group consisting of para-methyl, -methoxy, -chloro and -trifluoromethyl.

8. The method according to claim 4, comprising the administration of compounds wherein R" is selected from meta'- and para-fluoro provided that R' is ortho-fluoro.

9. The method according to claim 2, comprising the administration of compounds wherein $R_{41}$ is selected from hydrogen and sodium.

10. The method according to claim 2, comprising the administration of the compound, N-ethyl-N-phenyl-1,2-dihydro-4-hydroxy-1,5-dimethyl-2-oxo-quinoline-3-carboxamide.

11. The method according to claim 2, comprising the administration of the compound, N-ethyl-N-phenyl-1,2-dihydro-4-hydroxy-5-ethyl-1-methyl-2-oxo-quinoline-3-carboxamide.

12. The method according to claim 2, comprising the administration of the compound, N-ethyl-N-phenyl-1,2-dihydro-4-hydroxy-5-methoxy-1-methyl-2-oxo-quinoline-3-carboxamide.

13. The method according to claim 2, comprising the administration of the compound, N-ethyl-N-phenyl-1,2-dihydro-4-hydroxy-5-chloro-1-methyl-2-oxo-quinoline-3-carboxamide or its sodium salt.

14. The method according to claim 2, comprising the administration of the compound, N-ethyl-N-phenyl-1,2-dihydro-4-hydroxy-5-bromo-1-methyl-2-oxo-quinoline-3-carboxamide.

15. The method according to claim 2, comprising the administration of the compound, N-ethyl-N-phenyl-1,2-dihydro-4-hydroxy-5,6-methylenedioxy-1-methyl-2-oxo-quinoline-3-carboxamide.

16. The method according to claim 2, comprising the administration of the compound N-ethyl-N-phenyl-1,2-dihydro-4-hydroxy-5-dimethylamino-1-methyl-2-oxo-quinoline-3-carboxamide.

17. The method according to claim 2, comprising the administration of the compound, N-ethyl-N-(3-fluoro-phenyl)-1,2-dihydro-4-hydroxy-5-chloro-1-methyl-2-oxo-quinoline-3-carboxamide.

18. The method according to claim 2, comprising the administration of the compound N-methyl-N-(4-chloro-phenyl)-1,2-dihydro-4-hydroxy-5-chloro-1-methyl-2-oxo-quinoline-3-carboxamide.

19. The method according to claim 2, comprising the administration of the compound N-methyl-N-(4-methyl-phenyl)-1,2-dihydro-4-hydroxy-5-chloro-1-methyl-2-oxo-quinoline-3-carboxamide.

20. The method according to claim 2, comprising the administration of the compound, N-methyl-N-(2,4-difluoro-phenyl)-1,2-dihydro-4-hydroxy-5-chloro-1-methyl-2-oxo-quinoline-3-carboxamide.

21. The method according to claim 2, comprising the administration of the compound, N-methyl-N-(2,5-difluoro-phenyl)-1,2-dihydro-4-hydroxy-5-chloro-1-methyl-2-oxo-quinoline-3-carboxamide.

22. The method according to claim 2, comprising the administration of the compound, N-ethyl-N-(3-methoxy-phenyl)-1,2-dihydro-4-hydroxy-5-ethyl-1-methyl-2-oxo-quinoline-3-carboxamide.

23. The method according to claim 2, comprising the administration of the compound, N-methyl-N-(4-chloro-phenyl)-1,2-dihydro-4-hydroxy-1,5-dimethyl-2-oxo-quinoline-3-carboxamide.

24. The method according to claim 2, comprising the administration of the compound, N-methyl-N-(2,4-difluoro-phenyl)-1,2-dihydro-4-hydroxy-5-ethyl-1-methyl-2-oxo-quinoline-3-carboxamide.

25. The method according to claim 2, comprising the administration of the compound, N-methyl-N-(2,4-difluoro-phenyl)-1,2-dihydro-4-hydroxy-5-methoxy-1-methyl-2-oxo-quinoline-3-carboxamide.

26. The method according to claim 2, comprising the administration of the compound, N-methyl-N-(2,5-difluoro-phenyl)-1,2-dihydro-4-hydroxy-5-methoxy-1-methyl-2-oxo-quinoline-3-carboxamide.

27. The method according to claim 2, comprising the administration of the compound, N-methyl-N-(4-trifluoromethyl-phenyl)-1,2-dihydro-4-hydroxy-5-methoxy-1-methyl-2-oxo-quinoline-3-carboxamide.

28. The method according to claim 2, comprising the administration of the compound, N-methyl-N-(2,4-difluoro-phenyl)-1,2-dihydro-4-hydroxy-5,6-methylenedioxy-1-methyl-2-oxo-quinoline-3-carboxamide.

29. The method according to claim 2, comprising the administration of the compound, N-methyl-N-(4-methoxy-phenyl)-1,2-dihydro-5-dimethylamino-4-hydroxy-1-methyl-2-oxo-quinoline-3-carboxamide.

30. The method according to according to claim 3, comprising the administration of compounds wherein $R_5$ is selected from methyl, ethyl, methoxy, ethoxy, chloro, and bromo, or $R_5$ and $R_6$ taken together are methylenedioxy.

31. The method according to according to claim 3, comprising the administration of compounds wherein R is selected from methyl, ethyl, n-propyl.

32. The method according to according to claim 3, comprising the administration of compounds wherein R is hydrogen.

33. The method according to according to claim 3, comprising the administration of compounds wherein R is methyl and R' is hydrogen.

34. The method according to according to claim 3, comprising the administration of compounds wherein $R_{42}$ and $R_{43}$ are hydrogen.

35. The method according to according to claim 3, comprising the administration of compounds wherein R' is selected from the group consisting of hydrogen, para-methyl, -methoxy, -chloro, and -trifluoromethyl.

36. The compound according to claims 3, wherein R" is selected from the group consisting of metal'- and para-fluoro, provided that R' is ortho-fluoro.

37. The method according to according to claim 3, comprising the administration of the compound N-methyl-N-phenyl-4-amino-1,2-dihydro-1,5-dimethyl-2-oxo-quinoline-3-carboxamide.

38. The method according to according to claim 3, comprising the administration of the compound N-methyl-N-phenyl-4-amino-1,2-dihydro-5-methoxy-1-methyl-2-oxoquinoline-3-carboxamide.

39. The method according to according to claim 3, comprising the administration of the compound N-methyl-N-phenyl-1,2-dihydro-1,5-dimethyl-4-(N-methylamino)-2-oxo-quinoline-3-carboxamide.

40. The method according to according to claim 3, comprising the administration of the compound N-methyl-N-phenyl-1,2-dihydro-5-methoxy-4-(N-methylamino)-1-methyl-2-oxo-quinoline-3-carboxamide.

41. The method according to according to claim 3, comprising the administration of the compound N-methyl-N-(4-trifluoromethyl)phenyl-4-amino-1,2-dihydro-1-methyl-2-oxo-quinoline-3-carboxamide.

42. The method according to claim 1, for the treatment of prostatic cancers.

43. A compound of the formula (I')

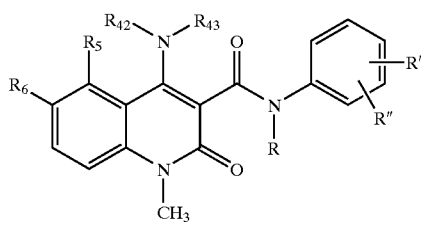

(I')

wherein
$R_{42}$ and $R_{43}$ are the same and different and selected from the group consisting of hydrogen, methyl, ethyl, n-propyl, iso-propyl, and cyclopropyl, or
$R_{42}$ is $COR_B$ wherein
$R_B$ is selected from C1–C4-alkyl, or
$COR_B$ is a 2-acyloxymethylbenzoyl group

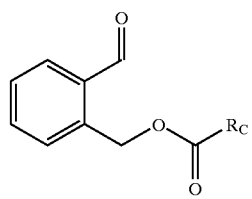

wherein
$R_C$ is selected from the group consisting of methyl, ethyl, phenyl and benzyl;
$R_{43}$ is as defined above;
R is selected from the group consisting of hydrogen, methyl, ethyl, n-propyl, iso-propyl, n-butyl, iso-butyl, sec.-butyl and allyl;
R' is selected from the group consisting of hydrogen, methyl, methoxy, fluoro, chloro, bromo, cyano, trifluoromethyl, and $OCH_xF_y$,
wherein
x=0–2,
y=1–3 with the proviso that
x+y=3;
R" is selected from the group consisting of hydrogen, fluoro and chloro, with the proviso that R" is selected from fluoro and chloro only when R' is selected from the group consisting of fluoro and chloro;
$R_5$ is selected from the group consisting of hydrogen, methyl, ethyl, n-propyl, iso-propyl, methoxy, ethoxy, fluoro, chloro, bromo, dimethylamino and $OCH_xF_y$, and $OCH_2CH_xF_y$,
wherein
x=0–2,
y=1–3 with the provisos that
x+y=3 and
that $R_5$ is hydrogen only when R' is trifluoromethyl;
$R_6$ is hydrogen; or
$R_5$ and $R_6$ taken together are methylenedioxy;
or any tautomer thereof.

44. A compound according to claim 43, wherein $R_5$ is selected from the group consisting of methyl, ethyl, methoxy, ethoxy, and $R_5$ and $R_6$ taken together are methylenedioxy.

45. The compound according to claim 43, wherein R is selected from the group consisting of methyl, ethyl, n-propyl.

46. The compound according to claim 43, wherein R is hydrogen.

47. The compound according to claim 43, wherein R is methyl and R' is hydrogen.

48. The compound according to claim 43, wherein $R_{42}$ and $R_{43}$ are hydrogen.

49. The compound according to claim 43, wherein R' is selected from the group consisting of hydrogen and para-trifluoromethyl.

50. The compound according to claims 43, wherein R" is selected from the group consisting of meta'- and para-fluoro provided that R' is ortho-fluoro.

51. The compound according to claim 43, N-methyl-N-phenyl-4-amino-1,2-dihydro-1,5-dimethyl-2-oxo-quinoline-3-carboxamide.

52. The compound according to claim 43, N-methyl-N-phenyl-4-amino-1,2-dihydro-5-methoxy-1-methyl-oxo-quinoline-3-carboxamide.

53. The compound according to claim 43, N-methyl-phenyl-5-chloro-1,2-dihydro-4-(N-methylamino)-1-methyl-2-oxo-quinoline-3-carboxamide.

54. The compound according to claim 43, N-methyl-N-(4-trifluoromethyl)-phenyl-4-amino-1,2-dihydro-1-methyl-2-oxo-quinoline-3-carboxamide.

55. The compound according to claim 43, N-methyl, N-phenyl-1,2-dihydro-1,5-dimethyl-4-(N-methylamino)-2-oxo-quinoline-3-carboxamide.

56. The compound according to claim 43, N-methyl-N-phenyl-1,2-dihydro-5-methoxy-4-(N-methylamino)-1-methyl-2-oxo-quinoline-3-carboxamide.

57. A therapeutic composition comprising the compound according to claim 43 and a pharmaceutically acceptable carrier or excipient.

58. A compound of the formula (I")

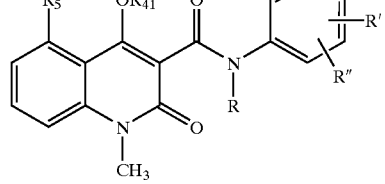

(I")

wherein
R is selected from the group consisting of ethyl, n-propyl, iso-propyl, n-butyl, iso-butyl, sec.-butyl and allyl;

$R_{41}$ is selected from the group consisting of hydrogen and pharmaceutically acceptable inorganic cations, and organic cations; and $COR_A$ wherein
$R_A$ is selected from alkyl and aryl groups;
R' and R" are hydrogen;
$R_5$ is dimethylamino;
or any tautomer, thereof.

59. The compound according to claim 58, N-ethyl-N-phenyl-1,2-dihydro-4-hydroxy-5-dimethylamino-1-methyl-2-oxo-quinoline-3-carboxamide.

60. A therapeutic composition comprising the compound according to claim 58, and a pharmaceutically acceptable carrier or excipient.

61. A method for the treatment of breast or prostatic cancer by the administration of a pharmaceutical composition comprising an amount effective therefor as active ingredient of a compound having the formula (I)

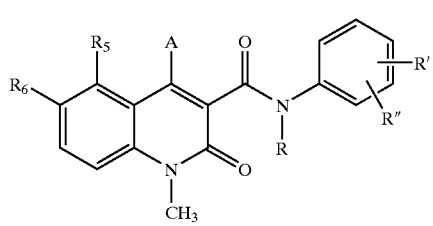

wherein
A is selected from the group consisting of $OR_{41}$ and $NR_{42}R_{43}$ wherein
$R_{41}$ is selected from the group consisting of hydrogen and pharmaceutically acceptable inorganic cations, and organic cations; and $COR_A$ wherein
$R_A$ is selected from the group consisting of alkyl and aryl groups;
$R_{42}$ and $R_{43}$ are the same or different and selected from the group consisting of hydrogen, methyl, ethyl, n-propyl, iso-propyl, cyclopropyl, or
$R_{42}$ is $COR_B$ wherein
$R_B$ is selected from C1–C4-alkyl, or
$COR_B$ is a 2-acyloxymethylbenzoyl group

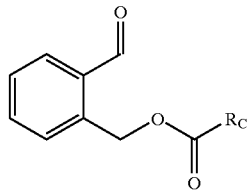

wherein
$R_C$ is selected from the group consisting of methyl, ethyl, phenyl and benzyl;
R is selected from the group consisting of hydrogen, methyl, ethyl, n-propyl, iso-propyl, n-butyl, iso-butyl, sec.-butyl and allyl; with the proviso that R is not hydrogen when A is $OR_{41}$;
R' is selected from the group consisting of hydrogen, methyl, methoxy, fluoro, chloro, bromo, cyano, trifluoromethyl, and $OCH_xF_y$,
wherein
x=0–2,
y=1–3 with the proviso that
x+y=3;
and with the proviso that R' is not hydrogen when R is methyl and A is $OR_{41}$;

R" is selected from the group consisting of hydrogen, fluoro and chloro, with the proviso that R" is selected from fluoro and chloro only when R' is selected from the group consisting of fluoro and chloro;

$R_5$ is selected from the group consisting of hydrogen, methyl, ethyl, n-propyl, iso-propyl, methoxy, ethoxy, fluoro, chloro, bromo, dimethylamino and $OCH_xF_y$, and $OCH_2CH_xF_y$
wherein
x=0–2,
y=1–3 with the proviso that
x+y=3 and with the further provisos that $R_5$ is not fluoro when A is $OR_{41}$; and that $R_5$ is hydrogen only when A is $NR_{42}R_{43}$ and R' is trifluoromethyl;

$R_6$ is hydrogen; or
$R_5$ and $R_6$ taken together are methylenedioxy;

or any tautomer thereof;

together with a pharmaceutically acceptable carrier.

62. The method according to claim 61, comprising the administration of the pharmaceutical composition in combination with other therapeutically active substances.

63. The method according to claim 61, comprising the administration of the pharmaceutical composition to a mammal in need thereof for the treatment of malignant tumours in dosage form sufficient to provide a daily dosage of the active substance of 0.002 mg/kg to about 100 mg/kg body weight.

64. A process for the preparation of a compound according to claim 43 by reaction of a 4-chloro-1,2-dihydro-2-oxo-quinoline-3-carboxamide of formula (II)

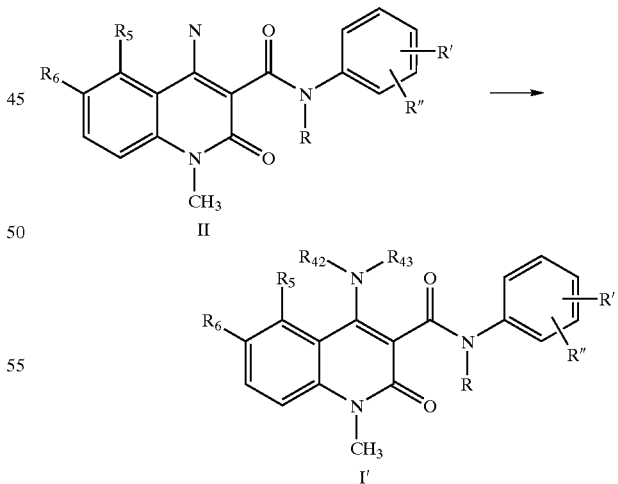

with an amino compound in a suitable solvent such as an alcohol, e.g., ethanol.

65. A process for the preparation of compounds according to claim 58 by reaction of an

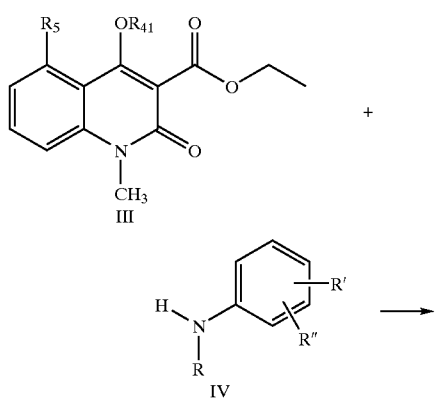
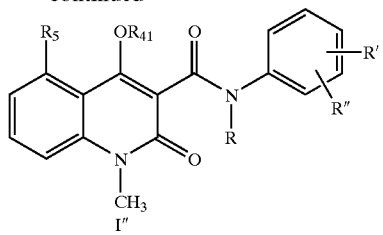
ester derivative of the quinoline carboxylic acid having formula III with an aniline of formula IV in a suitable solvent such as toluene, xylene and the like.
66. The method of claim 63 wherein said daily dosage is between 0.02 mg/kg to 10 mg/kg body weight.
* * * * *